(12) United States Patent
Seidel et al.

(10) Patent No.: US 6,270,960 B1
(45) Date of Patent: Aug. 7, 2001

(54) RECOMBINANT ANTIGEN FROM THE NS3 REGION OF THE HEPATITIS C VIRUS

(75) Inventors: Christoph Seidel, Weilheim; Ursula-Henrike Wienhues, Krailing; Urban Schmitt, Oberhausen; Manfred Motz, München; Michael Wiedmann, Penzberg; Barbara Upmeier, Iffeldorf; Erwin Soutschek, Berg, all of (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/592,197

(22) Filed: Jun. 12, 2000

Related U.S. Application Data

(62) Division of application No. 08/511,759, filed on Aug. 7, 1995, now Pat. No. 6,096,319.

(30) Foreign Application Priority Data

Aug. 12, 1994 (DE) .................................. 44 28 705

(51) Int. Cl.⁷ ............................ C12Q 1/70; G01N 33/53; G01N 33/566; C12P 21/04; A61K 38/00; C07K 1/00
(52) U.S. Cl. ............................... 435/5; 435/7.1; 435/7.2; 435/7.92; 435/69.3; 435/69.7; 435/69.8; 436/501; 530/300; 530/350; 424/189.1; 424/228.1
(58) Field of Search .................... 435/69.635, 7.2, 435/7.92, 7.1, 69.7, 69.8; 530/300, 350; 436/501

(56) References Cited

U.S. PATENT DOCUMENTS 5,371,017 * 12/1994 Houghton et al. ................ 435/320.1

FOREIGN PATENT DOCUMENTS

0450931-A1 * 9/1991 (EP) .

OTHER PUBLICATIONS

Mori et al. 1992. Serodiagnostic assay of Hepatitis C Virus infection using viral proteins expressed in *Escherichia coli*. Jpn. J. Cancer Research. vol. 83, pp. 264–268.*

Yang et al. 1994. cDNA cloning of c33–c antigen gene derived from NS3 region of Chinese HCV genome, expression in *Escherichia coli* and development of HCV EIA second–generation diagnostic kit. Science in China. vol. 37. No. 2, pp. 190–202.*

Choo et al. 1991. Genetic organization and diversity of the Hepatitis C virus. Proc. Natl. Acad. Sci. USA vol. 88, pp. 2451–2455.*

* cited by examiner

*Primary Examiner*—Mary E. Mosher
*Assistant Examiner*—Shanon Foley
(74) *Attorney, Agent, or Firm*—Fulbright & Jaworski, LLP

(57) ABSTRACT

The present invention concerns a polypeptide which is composed of the amino acids $1207\pm10$ to $1488\pm10$ of a hepatitis C virus and of less than 20 foreign amino acids and the use of this polypeptide as an antigen in an immunological test.

15 Claims, No Drawings

SEQUENCE LISTING

```
(1) GENERAL INFORMATION:

(iii) NUMBER OF SEQUENCES:   9

(2) INFORMATION FOR SEQ ID NO:    1:

(i) SEQUENCE CHARACTERISTICS:
        (A) LENGTH:   885 base pairs
        (B) TYPE:   nucleic acid
        (C) STRANDEDNESS:   both
        (D) TOPOLOGY:   linear (ii) MOLECULE TYPE:   cDNA (vi) ORIGINAL SOURCE:
        (A) ORGANISM: hepatitis C virus (viii) POSITION IN GENOME:
        (A) CHROMOSOME/SEGMENT:   NS3
```

(ix) FEATURE:
    (A) NAME/KEY: CDS
    (B) LOCATION: 1..885

(xi) SEQUENCE DESCRIPTION: SEQ ID NO: 1:

```
ATG ACC ATG ATT ACG AAT TCC CGG GGA TCC ATC ATG AAA TCC CCG GTG     48
Met Thr Met Ile Thr Asn Ser Arg Gly Ser Ile Met Lys Ser Pro Val
 1               5                  10                  15

TTC ACG GAT AAC TCC TCT CCA CCG GTA GTG CCC CAG AGC TTC CAG GTG     96
Phe Thr Asp Asn Ser Ser Pro Pro Val Val Pro Gln Ser Phe Gln Val
                20                  25                  30

GCT CAC CTG CAT GCT CCC ACA GGC AGC GGC AAG AGC ACC AAG GTC CCG    144
Ala His Leu His Ala Pro Thr Gly Ser Gly Lys Ser Thr Lys Val Pro
            35                  40                  45

GCT GCA TAC GCA GCT CAG GGC TAC AAG GTG CTA GTG CTC AAC CCT TCT    192
Ala Ala Tyr Ala Ala Gln Gly Tyr Lys Val Leu Val Leu Asn Pro Ser
        50                  55                  60

GTT GCT GCA ACA TTG GGC TTT GGT GCC TAC ATG TCC AAG GCT CAT GGG    240
Val Ala Ala Thr Leu Gly Phe Gly Ala Tyr Met Ser Lys Ala His Gly
 65                  70                  75                  80

ATC GAT CCT AAC ATC AGG ACC GGG GTG AGA ACA ATT ACC ACT GGC AGC    288
Ile Asp Pro Asn Ile Arg Thr Gly Val Arg Thr Ile Thr Thr Gly Ser
                85                  90                  95

CCC ATT ACG TAC TCC ACT TAC GGC AAG TTT CTT GCC GAC GGC GGG TGC    336
Pro Ile Thr Tyr Ser Thr Tyr Gly Lys Phe Leu Ala Asp Gly Gly Cys
            100                 105                 110

GCA GGG GGT GCT TAT GAC ATA ATA ATT TGT GAC GAG TGC CAC TCC ACG    384
Ala Gly Gly Ala Tyr Asp Ile Ile Ile Cys Asp Glu Cys His Ser Thr
        115                 120                 125

GAT GCC ACA TCC ATC TTG GGC ATC GGC ACT GTC CTT GAC CAA GGA GAG    432
Asp Ala Thr Ser Ile Leu Gly Ile Gly Thr Val Leu Asp Gln Gly Glu
130                 135                 140

ACT GCG GGG GCG AAA TTG GTT GTG TTC GCC ACC GCC ACC CCT CCG GGC    480
Thr Ala Gly Ala Lys Leu Val Val Phe Ala Thr Ala Thr Pro Pro Gly
145                 150                 155                 160

TCC GTC ACT GTG CCC CAT CCC AAC ATT GAG GAG GTT GCT CTA TCC ACC    528
Ser Val Thr Val Pro His Pro Asn Ile Glu Glu Val Ala Leu Ser Thr
                165                 170                 175

ACC GGA GAG ATC CCT TTT TAC GGC AAG GCT ATC CCC CTT GAG GTA ATC    576
Thr Gly Glu Ile Pro Phe Tyr Gly Lys Ala Ile Pro Leu Glu Val Ile
            180                 185                 190

AAG GGG GGG AGA CAT CTC ATC TTC TGT CAT TCA AAG AGG AAG TGC GAT    624
Lys Gly Gly Arg His Leu Ile Phe Cys His Ser Lys Arg Lys Cys Asp
        195                 200                 205

GAG CTC GCC ACA AAG CTG GTC GCA ATG GGC ATC AAT GCC GTG GCC TAC    672
Glu Leu Ala Thr Lys Leu Val Ala Met Gly Ile Asn Ala Val Ala Tyr
    210                 215                 220

TAC CGC GGT CTT GAC GTG TCC GTC ATC CCG ACC AGC GGT GAT GTT GTC    720
Tyr Arg Gly Leu Asp Val Ser Val Ile Pro Thr Ser Gly Asp Val Val
225                 230                 235                 240

GTC GTG GCA ACC GAC GCC CTC ATG ACC GGC TAT ACC GGC GAC TTC GAC    768
Val Val Ala Thr Asp Ala Leu Met Thr Gly Tyr Thr Gly Asp Phe Asp
                245                 250                 255

TCG GTG ATA GAC TGC AAC ACG TGT GTC ACT CAG ACA GTC GAT TTC AGC    816
Ser Val Ile Asp Cys Asn Thr Cys Val Thr Gln Thr Val Asp Phe Ser
            260                 265                 270

CTT GAC CCT ACC TTC ACC ATT GAG ACG ACC ACA CTT CCC CAG GAT GCT    864
Leu Asp Pro Thr Phe Thr Ile Glu Thr Thr Thr Leu Pro Gln Asp Ala
        275                 280                 285

GTC TCC CGC ACT CAA CGA CGG                                        885
```

Val Ser Arg Thr Gln Arg Arg
290                 295

(2) INFORMATION FOR SEQ ID NO:    2:

(i) SEQUENCE CHARACTERISTICS:
        (A) LENGTH: 295 amino acids
        (B) TYPE: amino acid
        (D) TOPOLOGY: linear (ii) MOLECULE TYPE: protein (xi) SEQUENCE DESCRIPTION:    SEQ ID NO: 2:

Met Thr Met Ile Thr Asn Ser Arg Gly Ser Ile Met Lys Ser Pro Val
1               5                   10                  15

Phe Thr Asp Asn Ser Ser Pro Val Val Pro Gln Ser Phe Gln Val
            20                  25                  30

Ala His Leu His Ala Pro Thr Gly Ser Gly Lys Ser Thr Lys Val Pro
        35                  40                  45

Ala Ala Tyr Ala Ala Gln Gly Tyr Lys Val Leu Val Leu Asn Pro Ser
50                  55                  60

Val Ala Ala Thr Leu Gly Phe Gly Ala Tyr Met Ser Lys Ala His Gly
65                  70                  75                  80

Ile Asp Pro Asn Ile Arg Thr Gly Val Arg Thr Ile Thr Thr Gly Ser
                85                  90                  95

Pro Ile Thr Tyr Ser Thr Tyr Gly Lys Phe Leu Ala Asp Gly Gly Cys
                100                 105                 110

Ala Gly Gly Ala Tyr Asp Ile Ile Cys Asp Glu Cys His Ser Thr
            115                 120                 125

Asp Ala Thr Ser Ile Leu Gly Ile Gly Thr Val Leu Asp Gln Gly Glu
    130                 135                 140

Thr Ala Gly Ala Lys Leu Val Val Phe Ala Thr Ala Thr Pro Pro Gly
145                 150                 155                 160

Ser Val Thr Val Pro His Pro Asn Ile Glu Glu Val Ala Leu Ser Thr
                165                 170                 175

Thr Gly Glu Ile Pro Phe Tyr Gly Lys Ala Ile Pro Leu Glu Val Ile
            180                 185                 190

Lys Gly Gly Arg His Leu Ile Phe Cys His Ser Lys Arg Lys Cys Asp
        195                 200                 205

Glu Leu Ala Thr Lys Leu Val Ala Met Gly Ile Asn Ala Val Ala Tyr
210                 215                 220

Tyr Arg Gly Leu Asp Val Ser Val Ile Pro Thr Ser Gly Asp Val Val
225                 230                 235                 240

Val Val Ala Thr Asp Ala Leu Met Thr Gly Tyr Thr Gly Asp Phe Asp
                245                 250                 255

Ser Val Ile Asp Cys Asn Thr Cys Val Thr Gln Thr Val Asp Phe Ser
                260                 265                 270

Leu Asp Pro Thr Phe Thr Ile Glu Thr Thr Thr Leu Pro Gln Asp Ala
            275                 280                 285

Val Ser Arg Thr Gln Arg Arg
290                 295

(2) INFORMATION FOR SEQ ID NO:    3:

(i) SEQUENCE CHARACTERISTICS:
        (A) LENGTH: 40 base pairs
        (B) TYPE: nucleic acid
        (C) STRANDEDNESS: single (D) TOPOLOGY: linear (ii) MOLECULE TYPE: cDNA (xi) SEQUENCE DESCRIPTION:    SEQ ID NO: 3:

AAGGGATCCA TCATGAAATC CCCGGTGTTC ACGGATAACT                              40

(2) INFORMATION FOR SEQ ID NO:    4:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION:    SEQ ID NO: 4:

GGGAAGCCTT AATTCTTACC GTCGTTGAGT GCGGGAGAC                               39

(2) INFORMATION FOR SEQ ID NO:    5:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION:    SEQ ID NO: 5:

GAGGGATCCA TCATGAAAGC GGTGGACTTT ATCCCTGTG                               39

(2) INFORMATION FOR SEQ ID NO:    6:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION:    SEQ ID NO: 6:

GAGAAGCTTT TAACACGTGT TGCAGTCTAT CAC                                    33

(2) INFORMATION FOR SEQ ID NO:    7:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION:    SEQ ID NO: 7:

GAGGGATCCA TCATGAAACA CCTGCATGCT CCCACCGGC                               39

(2) INFORMATION FOR SEQ ID NO:    8:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 8:

GAGAAGCTTT TAATACCAAG CACAGCCTGC GTC        33

(2) INFORMATION FOR SEQ ID NO: 9:

(i) SEQUENCE CHARACTERISTICS:
        (A) LENGTH: 302 amino acids
        (B) TYPE: amino acid
        (D) TOPOLOGY: linear (ii) MOLECULE TYPE: protein (xi) SEQUENCE DESCRIPTION: SEQ ID NO: 9:

```
Pro Val Glu Asn Leu Glu Thr Thr Met Arg Ser Pro Val Phe Thr
 1               5                  10                  15

Asp Asn Ser Ser Pro Pro Val Val Pro Gln Ser Phe Gln Val Ala
                20                  25                  30

His Leu His Ala Pro Thr Gly Ser Gly Lys Ser Thr Lys Val Pro
                35                  40                  45

Ala Ala Tyr Ala Ala Gln Gly Tyr Lys Val Leu Val Leu Asn Pro
                50                  55                  60

Ser Val Ala Ala Thr Leu Gly Phe Gly Ala Tyr Met Ser Lys Ala
                65                  70                  75

His Gly Ile Asp Pro Asn Ile Arg Thr Gly Val Arg Thr Ile Thr
                80                  85                  90

Thr Gly Ser Pro Ile Thr Tyr Ser Thr Tyr Gly Lys Phe Leu Ala
                95                 100                 105

Asp Gly Gly Cys Ala Gly Gly Ala Tyr Asp Ile Ile Ile Cys Asp
               110                 115                 120

Glu Cys His Ser Thr Asp Ala Thr Ser Ile Leu Gly Ile Gly Thr
               125                 130                 135

Val Leu Asp Gln Gly Glu Thr Ala Gly Ala Lys Leu Val Val Phe
               140                 145                 150

Ala Thr Ala Thr Pro Pro Gly Ser Val Thr Val Pro His Pro Asn
               155                 160                 165

Ile Glu Glu Val Ala Leu Ser Thr Thr Gly Glu Ile Pro Phe Tyr
               170                 175                 180

Gly Lys Ala Ile Pro Leu Glu Val Ile Lys Gly Gly Arg His Leu
               185                 190                 195

Ile Phe Cys His Ser Lys Arg Lys Cys Asp Glu Leu Ala Thr Lys
               200                 205                 210

Leu Val Ala Met Gly Ile Asn Ala Val Ala Tyr Tyr Arg Gly Leu
               215                 220                 225

Asp Val Ser Val Ile Pro Thr Ser Gly Asp Val Val Val Val Ala
               230                 235                 240

Thr Asp Ala Leu Met Thr Gly Tyr Thr Gly Asp Phe Asp Ser Val
               245                 250                 255

Ile Asp Cys Asn Thr Cys Val Thr Gln Thr Val Asp Phe Ser Leu
               260                 265                 270

Asp Pro Thr Phe Thr Ile Glu Thr Thr Thr Leu Pro Gln Asp Ala
               275                 280                 285

Val Ser Arg Thr Gln Arg Arg Gly Arg Thr Gly Arg Gly Lys Pro
               290                 295                 300

Gly Ile
 302
```

RECOMBINANT ANTIGEN FROM THE NS3 REGION OF THE HEPATITIS C VIRUS

PRIOR APPLICATION

This application is a divisional of Ser. No. 08/511,759, filed Aug. 7, 1995, now U.S. Pat. No. 6,096,319.

DESCRIPTION

The invention concerns polypeptides from the non-structural protein 3 (NS3) region of the hepatitis C virus (HCV), a nucleic acid coding for such polypeptides as well as the use of the polypeptide as an antigen in an immunological test procedure or as helicase protein.

The disease denoted non-A-non-B hepatitis is caused in many cases by the hepatitis C virus (HCV). HCV is a single-stranded encapsulated RNA virus whose genome is composed of about 9 to 10,000 bases. This genome codes for structural proteins (core and envelope proteins) as well as for non-structural proteins. The non-structural protein 3 (NS3) region of HCV contains a protease and a helicase. The protease activity is localized in the amino terminal third of the NS3 region.

A partial nucleotide sequence of HCV is disclosed in the European Patent Application EP-A-0 318 216. It claims the use of nucleic acid fragments or polypeptide sections from HCV for a diagnostic test and for therapeutic treatment.

EP-A-0 450 931 incorporated by reference discloses the complete nucleotide and amino acid sequence of HCV. In addition a combination of synthetic HCV antigens is described comprising a first HCV antigen from the C domain and at least one further HCV antigen from one of the non-structural domains NS3, NS4 or NS5 and the envelope domain S. A preferred antigen from the domain NS3 is an antigen denoted C33c which comprises the amino acids 1192 to 1457 encoded by the HCV genome shown in FIG. 1 of EP-A-0 450 931.

The international Patent Application WO92/11370 concerns the cloning and sequencing of various polypeptides from the genome of HCV and the use of these polypeptides without any foreign protein parts in test kits and as a vaccine. A clone NS-3 deposited in connection with this application at the "Deutsche Sammlung für Mikroorganismen und Zellkulturen GmbH, Mascheroder Weg 1b, 38124 Braunschweig, BRD (DSM)" under the number 6847 contains the genetic information for a polypeptide of 527 amino acids from the NS3 region of HCV.

Mori et al., (Jpn. J. Cancer Res. 83 (1992), 264–268) describes the diagnostic detection of a HCV infection by determining viral antibodies in blood using viral proteins as antigens. These HCV proteins are expressed in *E. coli* as a fusion protein with β-galactosidase. A protein from the NS3 region containing the amino acids 1295 to 1541 of the HCV genome showed the highest sensitivity. However, a disadvantage of such fusion proteins is that cross-reactions with the fused protein part can occur which reduce the specificity of the test reaction.

A test for HCV in blood requires a high degree of specificity and sensitivity. Furthermore the antigen used for the test should be capable of expression in high yield and be stable. Previously known antigens from the HCV genome have disadvantages since they do not fulfil one or several of the above requirements.

Thus an object of the present invention is to provide a polypeptide encoded by the HCV genome in which these disadvantages of the state of the art are at least partially eliminated and which, especially in comparison with known antigens, has a higher specificity and sensitivity and can be expressed in higher yield and is stable.

This object is achieved by a polypeptide which is composed of amino acids 1207±10 to 1488±10 of a hepatitis C virus and has less than 20, preferably less than 15 foreign amino acids. The polypeptide according to the invention preferably contains the amino acids 1207±5 to 1488±5. More preferably they contain amino acids particularly preferably 1207±2 to 1488±2 and most preferably 1207 to 1488 of hepatitis C virus in which the numbering of the amino acid residues refers to FIG. 1 of EP-A-0 450 931 incorporated by reference.

The polypeptide according to the invention can be derived from an arbitrary HCV isolate, for example from a HCV isolate with a nucleotide sequence as described in EP-A-0 450 931. However, the polypeptide is preferably derived from the HCV isolate from which the clone NS3 described in WO92/11370 is derived which was deposited at the "Deutsche Sammlung von Mikroorganismen und Zellkulturen GmbH" (DSM), Mascheroder Weg 1b, 38124 Braunschweig, under the number DSM 6847. The polypeptide according to the invention is preferably obtained by recombinant expression of the vector pUC-D26.

SEQ ID NO: 1 shows the amino acid sequence of a polypeptide according to the invention. Amino acids 1–13 are foreign amino acids. Amino acids 14–295 originate from HCV. The polypeptide according to the invention preferably contains amino acids 14–295 of the amino acid sequence shown in SEQ ID NO: 1 and 2 or an amino acid sequence which is at least 90% homologous thereto.

The present invention also concerns a polypeptide defined as above which contains at least one marker group. All known marker groups come into consideration as the marker group that can be detected in a test system i.e. directly or indirectly detectable marker groups. In this connection a directly detectable marker group is understood as a group which produces a directly detectable signal e.g. a radioactive group, an enzyme group, a luminescence group, a metal complex etc. On the other hand the marker group can also be an indirectly detectable group e.g. a biotin or hapten group that is detectable by reaction with a suitable binding partner (streptavidin, avidin or anti-hapten antibody) which in turn carries a signal-generating group. The marker group can be coupled in known manner to the antigen for example via a bifunctional spacer. Such processes for coupling marker groups to peptide antigens are known to a person skilled in the area of immunology and do not need to be described in detail here.

The polypeptide according to the invention preferably contains 1 to 12 and particularly preferably 3 to 7 marker groups.

In addition, the invention concerns a polypeptide as defined above in which one or several of the sulfhydryl groups of cysteine residues are present in covalently modified form. Examples of suitable covalent modifying groups are maleimidodioxaoctylamine (MADOO), N-methylmaleinimide (NMM), iodoacetic acid and iodoacetamide. The covalent cysteine modification results in particularly high specific immunological reactivity.

Directly or indirectly detectable marker groups are preferably covalently coupled to the sulfhydryl groups of the polypeptide. Examples of SH-reactive bifunctional linkers for coupling to sulfhydryl groups are maleimidopropylamine (MP), maleimidoethylamine (MEA) and maleimidodioxaoctylamine (MADOO).

In addition, it may be preferable to use a polypeptide according to the invention in which one or several cysteine residues are replaced by other natural or artificial amino acids. Cysteine residues are preferably replaced by structurally analogous α-amino acids e.g. serine or α-aminobutyric acid. Cysteine substitutions lead to particularly high stability.

The polypeptide according to the invention has surprising advantages over already known polypeptides. Compared to the antigen C33 described in EP-A-0 450 931 which contains the amino acid residues 1192 to 1457 of the HCV sequence, the polypeptides according to the invention exhibit substantially higher specificity which is manifested in a statistically significant lower number of false positive results in negative sera. Compared to the antigen NS3 described in WO92/11370 which contains the region of amino acids 1007 to 1534 of the HCV sequence, the polypeptide according to the invention has considerably higher stability under test conditions. Compared to a polypeptide which contains amino acids 1227 to 1528 from the NS3 region of HCV, the polypeptide according to the invention has the advantage of improved expression efficiency and a higher sensitivity. Due to these advantages the polypeptides according to the invention are substantially superior to all previously known HCV antigens from the NS3 region.

In addition, the invention concerns an isolate nucleic acid which codes for a polypeptide according to the invention. A preferred example of such a nucleic acid is a foreign DNA encoding the peptide of interest inserted in the vector pUC-D26.

SEQ ID NO: 1 also shows the nucleotide sequence of a nucleic acid according to the invention which codes for the polypeptides of SEQ ID NO: 1 and 2. Nucleotides 40–885 code for the region of the polypeptide derived from HCV. The nucleic acid according to the invention preferably contains (a) nucleotides 40–885 of the nucleotide sequence shown in SEQ ID NO.1 or (b) a nucleotide sequence that corresponds to a sequence from (a) within the scope of the degeneracy of the genetic code.

The present invention also concerns a vector which contains at least one copy of a nucleic acid according to the invention. The vector according to the invention is preferably a prokaryotic vector i.e. a vector suitable for propagation in a prokaryotic host cell. Examples of such vectors are shown in Sambrook et al. (Molecular Cloning. A Laboratory Manual, 2nd Ed., Cold Spring Harbor Laboratory Press (1989)), especially in chapters 1 to 4 and 17. The vector according to the invention is preferably a circular plasmid. The nucleic acid according to the invention is preferably present on the vector under the control of a promoter sequence which allows expression of the polypeptide according to the invention. A preferred example of a vector according to the invention is pUC-D26.

Furthermore the invention concerns a cell which is transformed with at least one copy of a nucleic acid according to the invention or with a vector according to the invention. The cell is preferably a prokaryotic cell, more preferably a gram-negative prokaryotic cell and most preferably an *E. coli* cell.

The polypeptide according to the invention is preferably used as an antigen in an immunological test procedure. On the other hand the polypeptide can, however, also be used as a helicase protein and, due to its excellent antigenic action, for the production of a vaccine against HCV infection.

The present invention additionally concerns a method for the immunological determination of an antibody directed towards a hepatitis C virus in a sample liquid which is characterized in that the sample liquid is incubated with at least one polypeptide according to the invention and the antibody is detected via binding to the polypeptide. This immunological method of determination can be carried out using any known test format e.g. in a homogeneous immunoassay with a single reaction phase or in a heterogeneous immunoassay with more than one reaction phase. A heterogeneous test format is preferably used in which the presence of the antibody is detected in the presence of a reactive solid phase.

One embodiment of this test format is the so-called double antigen bridge test concept. In such a method the sample liquid is incubated with at least two polypeptides $P_1$ and $P_2$ according to the invention in which polypeptide $P_1$ (a) is bound to a solid phase or (b) is present in a form capable of binding to a solid phase and polypeptide $P_2$ carries a marker group. The antibody in the sample liquid is detected by determining the label in the solid phase or/and in the liquid phase, preferably in the solid phase, by means of an immobilized complex i.e. one that is bound to the solid phase.

The test procedure preferably comprises mixing the sample liquid with a purified labelled antigen $P_2$ and with the purified solid phase antigen $P_1$ in order to obtain a labelled immobilized complex consisting of labelled antigen, antibody and solid phase-bound antigen. Compared to other test formats for detecting antibodies, the bridge test format leads to an improvement of the sensitivity of the assay, i.e. additional immunoglobulin classes such as IgM are recognized, and of the specificity, i.e., unspecific reactivities with anti-IgG conjugate are reduced.

The labelled antigen $P_2$ carries a directly or indirectly detectable marker group as described above. The solid phase antigen $P_1$ can be found for example directly to the solid phase via a bifunctional spacer. However, $P_1$ is preferably a conjugate present in the solid phase of a polypeptide according to the invention and of a reaction partner of a specific binding system. The other reaction partner of the specific binding system is present bound to the solid phase. Examples of such specific binding systems are biotin/avidin, biotin/streptavidin, biotin/antibiotin, hapten/antihapten, carbohydrate/lectin and antibody or antibody fragment and antibody against this antibody or against the antibody fragment. The antigen $P_1$ is preferably in the form of a biotin conjugate.

In such a double antigen bridge test the polypeptide antigen according to the invention is preferably used in a soluble form in order to avoid increases in the blank value and an unfavourable signal/noise ratio due to aggregations of the antigen. For this purpose the antigen is already either expressed in a soluble form in a suitable expression system, or after expression in soluble form, it is renatured in vitro in a known manner. Furthermore in order to avoid the formation of covalently cross-linked molecular aggregates, the immunological test can be carried out under mild reducing conditions (addition of mild reducing reagents, preferably of sulfhydryl reagents, preferably DTT (dithiothreitol) or DTE (dithioerythritol) in a concentration range of 1 mmol/l to 25 mmol/l) or/and preferably an antigen with covalently modified sulfhydryl groups or/and an antigen with at least partially substituted cysteine residues is used.

The polypeptide antigen according to the invention is preferably used in a soluble form in such a double antigen bridge test in order to avoid increases in the blank and an unfavourable signal/noise ratio due to aggregations of the antigen. A detailed description of the bridge test format is given in EP-A-0 280 211. This patent application is incorporated by reference.

The polypeptide according to the invention can, however, also be used in other test formats. An example of this is an indirect immunoassay for recognizing a specific immunoglobulin by binding to an immobilized specific antigen and indirect detection via a conjugate with a second antibody. In this embodiment of the method according to the invention the sample liquid is incubated with a polypeptide $P_1$ which is (a) bound to a solid phase or (b) is present in a form capable of binding to a solid phase and with a further antibody directed towards $P_1$ which carries a marker group. The antibody to be determined is detected indirectly by determination of the label in the solid phase and/or in the liquid phase, preferably in the solid phase. In this method the signal produced on the solid phase by an immobilized complex of labelled antibody and solid phase-bound antigen is indirectly proportional to the concentration of the antibodies to be determined in the sample liquid.

The present invention also concerns a reagent for the immunological determination of an antibody directed towards hepatitis C virus which contains at least one polypeptide according to the invention. If the reagent is used in a double antigen bridge test, it preferably contains at least two polypeptides $P_1$ and $P_2$ wherein polypeptide $P_1$ is (a) bound to a solid phase or (b) is present in a form capable of binding to a solid phase and polypeptide $P_2$ carries a marker group. Binding of the polypeptide $P_1$ to the solid phase can either be achieved by direct binding or by means of a specific binding pair, preferably streptavidin/avidin and biotin. The polypeptide $P_1$ is particularly preferably present in a biotinylated form.

If it is used in an indirect immunological test the reagent according to the invention preferably contains a polypeptide $P_1$ which is (a) bound to a solid phase or (b) is present in a form capable of binding to a solid phase and an antibody directed against $P_1$ which carries a marker group. The production of antibodies directed towards the polypeptide according to the invention is carried out in a well-known manner by immunizing experimental animals with the corresponding antigen and isolating polyclonal antisera from the experimental animal. Alternatively a monoclonal antibody against the antigen can be produced by the method of Köhler and Milstein or a further development of this method. Antibody fragments or antibody derivatives can also be used instead of a complete antibody.

A further area of application of the polypeptide according to the invention is to produce vaccines. For this the polypeptides according to the invention are preferably produced in a purified form and then brought into the form of injectable liquids which can either be solutions or suspensions of the polypeptides. The polypeptides can also be enclosed in liposomes. Further constituents of these vaccines may include water, salt solutions, glucose or glycerol. In addition the vaccines may contain small amounts of auxiliary substances such as emulsifiers, buffer substances, and if necessary adjuvants which increase the immune response. The vaccines are usually administered parenterally by injection, preferably subcutaneously or intramuscularly.

Yet a further object of the present invention is a method for the immunological determination of an antibody directed towards a hepatitis C virus in a sample liquid in which the sample liquid is incubated with at least one polypeptide that contains sequence regions from the hepatitis C virus, in particular from the NS3 region of the hepatitis C virus, and the antibody is detected by binding to the polypeptide, which is characterized in that one uses a polypeptide from a region which contains at least one cysteine residue and (a) the antibody is determined under reducing conditions, (b) one or several cysteine residues are covalently modified or/and (c) one or several cysteine residues are replaced by other amino acids.

In contrast to other antigenic regions from HCV the NS3 region contains a particularly large accumulation of cysteine residues. Although the NS3 protein synthesized during the course of virus replication is stable, the use of NS3 antigens under physiological buffer conditions, e.g. in immunological test procedures, has proven to be extremely problematic since the free sulfhydryl groups of the cysteine residues easily oxidize under these conditions. This leads to intramolecular as well as intermolecular cross-linking of the antigen which significantly reduces its immunological reactivity.

Surprisingly it was possible to significantly improve the immunological reactivity of these NS3 antigens by means of a test format in which one or several NS3 antigens with modified cysteine residues or/and with substituted cysteine residues are used or mild reducing conditions are present for example by addition of a sulfhydryl reagent. In this way an early recognition of seroconversion is achieved as well as a significant amplification of the measurement signal.

The present invention is described further by the following examples and sequence protocols.

SEQ ID NO. 1: shows the nucleotide sequence of a preferred polypeptide according to the invention, SEQ ID NO. 2: shows the amino acid sequence of a preferred nucleic acid according to the invention, SEQ ID NO. 3: shows the nucleotide sequence of primer (1)

SEQ ID NO. 4: shows the nucleotide sequence of primer (2)

SEQ ID NO. 5: shows the nucleotide sequence of primer (3)

SEQ ID NO. 6: shows the nucleotide sequence of primer (4)

SEQ ID NO. 7: shows the nucleotide sequence of primer (5) and

SEQ ID NO. 8: shows the nucleotide sequence of primer (6).

EXAMPLES

Example 1

Cloning and Expression of a Polypeptide with Amino Acids 1207 to 1488 from the NS3 Region of the Hepatitis C Virus A DNA fragment was amplified by means of PCR starting with the clone NS3 (DSM 6847) using primers (1) and (2) whose nucleotide sequence is shown in SEQ ID NO. 3 and SEQ ID NO. 4. Sequences for cloning (BamHI, BspHI, EcoRI restriction cleavage sites) are located at the 5' end of this DNA fragment as well as an ATG codon and an AAA(Lys) codon to increase expression. Restricting sites for HindIII and EcoRI and a stop codon (TAA) are present at the 3' end. In primers (1) and (2) the region homologous to HCV starts at nucleotide No. 19.

The DNA fragment obtained in this way was used in a pUC8 vector cleaved with BamHI and HindIII. The resulting plasmid was denoted pUC-D26.

An *E. coli* strain JM109 (Yanisch-Perron et al., Gene 33 (1985), 103) transformed with plasmid pUC-D26 was incubated overnight in 100 ml medium (L broth/ampicillin).

Next morning the culture was diluted in a 3 l flask with 900 ml 2× L-broth (10 g tryptone, 10 g yeast extract, 5 g NaCl per liter)/ampicillin. After addition of 2 ml glycerol and 1 to 2 drops silicon anti-foam emulsion (Serva Company) the culture was then shaken at ca. 185 rpm and 37° C. for 2 hours. Induction and antigen production were achieved by adding 2 mmol/l of the inducer isopropylthio-β-D-galactoside (IPTG) and shaking further for 3 to 4 hours. Subsequently the bacteria were pelleted by centrifugation and processed further.

The bacterial pellets from two one liter cultures were resuspended in 200 ml 50 mmol/l Tris-HCl, pH 8.5, 0.2 mg/ml lysozyme and 2 mmol/l dithioerythritol (DTE). Subsequently EDTA (final concentration: 15 mmol/l), phenylmethylsulfonyl fluoride (final concentration: 1 mmol/l) and 4 mg DNase were added. The suspension was mixed for several minutes with a magnetic stirrer and incubated for 45 minutes at 37° C. in a water bath.

Afterwards Triton-X100 (final concentration: 1%) was added and it was stirred for 30 minutes in a magnetic stirrer. After freezing at −20° C. overnight and thawing, the cells were stirred for at least 1 hour at 37° C. and sonified if necessary. The incubation at 37° C. and/or ultrasonic treatment should be continued until the viscosity of the suspension of lysed cells has decreased significantly.

Subsequently this was centrifuged for 20 minutes at 35,000 g and 4° C. The resulting pellet was resuspended in 30 ml 50 mmol/l Tris-HCl, pH 8.5, 2 mmol/l DTE, 150 mmol/l EDTA and 1.5% OGP (oxtyl-β-D-glucopyranoside, Biomol Company). This suspension was stirred vigorously at room temperature with a magnetic stirrer for at least three hours and subsequently centrifuged at 35,000 g and 4° C. for 20 minutes.

The pellet was dissolved in 100 ml of 8 mol/l urea, 20 mmol/l Tris-HCl, pH 8.5, 2 mmol/l DTE and stirred. The antigen which was now dissolved, can be frozen at −20° C. until further processing.

The protein was purified by the chromatographic steps described infra which were carried out at room temperature. The antigen was stored between each of the chromatographic steps at −20° C.

The first chromatographic step was carried out on a Q-Sepharose Fast Flow column (Pharmacia) with a 20 mmol/l Tris-HCl pH 8.5, 8 mol/l urea, 2 mmol/l DTE buffer. It was eluted with a NaCl gradient (0 to 0.7 mol/l). The void volume and the fractions were tested by means of SDS PAGE. The polypeptide according to the invention is located in the first main peak. The positive fractions were pooled and dialyzed overnight against a 10-fold volume of 4 mol/l urea, 2 mmol/l DTE, 20 mmol/l Tris-HCl pH 7.3.

The same column was used in the second chromatographic step. The column buffer was the dialysis buffer used after the first chromatographic step. It was eluted using a NaCl gradient (0 to 0.5 mol/l) and subsequently with 1 mol/l NaCl, NaOH pH 13, 4 mol/l urea.

The positive fractions were pooled and dialyzed overnight against the same buffer as above.

Finally it was chromatographed on a S-Sepharose Past Flow column (Pharmacia). The buffer and elution conditions were the same as in the previous chromatographic step.

The antigen has a size of ca. 41 kDa on SDS polyacrylamide gel. The yield was ca. 10 mg antigen per liter culture medium.

Example 2

Expression of the Antigen According to the Invention in Comparison with Other Antigens from the HCV NS3 Region The following antigens were expressed:

a) antigen D26 according to the invention (amino acids 1207 to 1488)

b) antigen C33 (amino acids 1192 to 1457 according to EP-A 0 450 931)

c) antigen D27 (amino acids 1227 to 1528)

d) antigen NS3 (amino acids 1007–1534).

The antigen NS3 was expressed using the deposited clone NS-3 (DSM 6847). Cloning and expression of the antigens C33 and D27 were carried out according to the method described in example 1. The coding regions of amino acids 1192 to 1457 for C33 and amino acids 1227 to 1528 for D27 were amplified by standard methods using PCR starting with the plasmid pUC-N3 from the clone NS-3.

The primers (3) and (4) were used for C33 whose nucleotide sequences are shown in SEQ ID NO.5 and SEQ ID NO. 6. The primers (5) and (6) were used for D27 whose nucleotide sequences are shown in SEQ ID NO.7 and SEQ ID NO. 8. The region homologous to HCV starts at nucleotide No. 19 in primers (3) and (5) and at nucleotide No. 13 in primers (4) and (6).

After treatment with the restriction enzymes BamHI and HindIII and subsequent purification by agarose gel electrophoresis the amplified DNA fragments were inserted into the vector pUC8 that had been cleaved with BamHI and HindIII. Both antigens expressed by the pUC vectors have a region of 13 non HCV-coded foreign amino acids at the N-terminal end (Met-Thr-Met-Ile-Thr-Asn-Ser-Arg-Gly-Ser-Ile-Met-Lys).

Afterwards the plasmids were transformed in *E. coli* JM109. Clones which receive a DNA fragment coding for the C33 antigen express an antigen with a molecular weight of ca. 34 kDa (SDS-PAGE). In clones with a DNA fragment that codes for antigen D27, a band of 48 kDa is found.

In the case of C33 its percentage of the total protein is ca. 10% and is about the same magnitude as the polypeptide D26 according to the invention. A considerably smaller expression in the range of 5% or less is found for D27.

Lysates of clones expressing D26, D27 and C33 were concurrently separated in an SDS gel and transferred onto nitrocellulose. After incubating overnight with various HCV-positive sera in a 1:100 dilution, bound antibodies were detected by means of an anti-human IgG antibody-peroxidase conjugate and a colour reaction with 3,3'-diaminobenzidine tetrachloride (DAB)/hydrogen peroxide.

Good reactivity is found in all HCV antigen segments with strongly positive sera. In the case of weakly positive NS3-HCV sera the C33 antigen exhibits in some cases the same and in other cases a slightly weaker reactivity in comparison with the antigen according to the invention. However, in the case of D27 a considerably reduced colour reaction with weak NS3-positive sera is found.

Example 3

Investigation of the Specificity and Sensitivity of Various Antigens from the NS3 Region of HCV The reactivity of various antigens from the NS3 region was comparatively assessed on a total of 960 negative sera using the indirect test concept. In this evaluation the antigen D26 according to the invention was found to have a significantly superior specificity compared to the reference antigen C33 which manifesto itself as a significantly reduced number of false positive results.

| Construct | false positive classification | correct negative classification |
|---|---|---|
| C33 | 8 | 952 |
| D26 | 2 | 958 |

In addition the reactivity of various NS3 constructs was comparatively assessed using the indirect test concept on 20 sera of proven HCV status. A reduced sensitivity of antigen D27 was found with comparable sensitivity of the constructs NS3 (amino acids 1007 to 1534), C33, D26 and D27.

| Construct | correct positive classification | false negative classification |
|---|---|---|
| NS3 | 20 | 0 |
| C33 | 20 | 0 |
| D26 | 20 | 0 |
| D27 | 19 | 1 |

Example 4

Investigation of the Stability of Antigens from the NS3 Region of HCV

The stability of the antigens NS3 and D26 was comparatively evaluated using the indirect test concept. Antigen NS3 was found to have a significantly poorer stability compared to antigen D26 according to the invention. The stability of the antigens was investigated after 72 hours incubation at 37° C.

| Construct | Sample No. | Signal recovery |
|---|---|---|
| NS3 | 1 | <20% |
|  | 2 | <20% |
| D26 | 1 | 99% |
|  | 2 | 103% |

Example 5

Investigation of the Reactivity of the HCV-NS3 Helicase Antigen in the Presence or Absence of Reducing Reagents The time of seroconversion was tested on the bases of the reactivity of serum samples collected at various times with the HCV-NS3 helicase antigen under physiological conditions with or without 20 mmol/l DTT. The test concept was a double-antigen bridge test for the class-independent recognition of all immunoglobulins in which an antigen provided with an electrochemical marker group (ruthenium metal complex) and an antigen bindable to a solid phase (biotinylated antigen) was used.

The results of this test are shown in the following table. It can be seen that it was possible to recognize seroconversion 38 days earlier in the presence of 20 mmol/l DTT. In addition an improved signal strength was found in the presence of DTT.

TABLE

| Day of blood collection | Days after start of blood collection | Reactivity of the NS3 antigen without DTT (signal/cut off) | Reactivity of the NS3 antigen with DTT (signal/cut off) |
|---|---|---|---|
| 28.07.1988 | 0 | 0.1 | 0.1 |
| 01.08.1988 | 4 | 0.1 | 0.1 |
| 08.08.1988 | 11 | 0.1 | 0.1 |
| 11.08.1988 | 14 | 0.1 | 0.1 |
| 15.08.1988 | 18 | 0.1 | 0.1 |
| 25.08.1988 | 28 | 0.1 | 0.1 |
| 29.08.1988 | 32 | 0.1 | 1.6* |
| 14.09.1988 | 48 | 0.1 | 6.5* |
| 05.10.1988 | 69 | 1.3* | 4.8 * |
| 19.10.1988 | 83 | 2.1* | 6.8* |

*positive signal

---

What is claimed is:

1. A method for determining presence of hepatitis C virus specific antibodies in a sample, comprising contacting said sample with an isolated polypeptide, the amino acid sequence of which consists of (i) an amino acid sequence which is at least 90% identical to amino acids 14–295 of SEQ ID NO: 2 and (ii) an amino acid sequence of less than 20 amino acids which is not found in hepatitis C virus, wherein (ii) is concatenated to the N-terminus or to the C-terminus of the amino acid sequence of (i), and determining binding thereto as a determination of antibodies to hepatitis C virus in said sample.

2. The method of claim 1, wherein (i) consists of an amino acid sequence at least 90% identical to amino acids 14–295 of SEQ ID NO: 2.

3. A method for determining presence of hepatitis C virus specific antibodies in a sample, comprising contacting said sample with a polypeptide, the amino acid sequence of which consists of (i) an amino acid sequence which is at least 90% identical to a sequence of at least amino acids 1217–1478 and no more than amino acids 1197–1498 from an NS3 region of a hepatitis C virus and (ii) an amino acid sequence of less than 20 amino acids which is not found in hepatitis C virus and is concatenated to the N-terminus or the C-terminus of (i), and determining binding thereto as a determination of antibodies to hepatitis C virus in said sample.

4. The method of claim 3, wherein (i) consists of no less than amino acids 1217–1478 and no more than amino acids 1197–1498 of an NS3 region of a hepatitis C virus.

5. A method for determining presence of hepatitis C virus specific antibodies in a sample, comprising contacting said sample with an isolated polypeptide, the amino acid sequence of which consists of (i) at least amino acids 21–282 of SEQ ID NO: 9, and no more than amino acids 1–302 of SEQ ID NO: 9, and (ii) an amino acid sequence of less than 20 amino acids which is not found in hepatitis C virus, wherein (ii) is concatenated to the N-terminus or to the C-terminus of the amino acid sequence of (i), and determining binding thereto as a determination of antibodies to hepatitis C virus in said sample.

6. The method of claim 5, further comprising contacting said sample with a second polypeptide, wherein one of said polypeptides is bound to a solid phase or is bindable to a solid phase to form a complex of said polypeptide and antibody, and determining any antibody bound to said solid phase.

7. The method of claim 5, wherein said isolated polypeptide is bound to or is bindable to a solid phase, said method further comprising contacting said sample with a second, labelled antibody which binds to said polypeptide, and determining antibody in said sample indirectly by determining labelled antibody bound to said solid phase.

8. The method of claim 5, wherein said method is carried out under reducing conditions.

9. The method of claim 5, wherein the amino acid sequence derived from hepatitis C virus consists of no less than amino acid 16–287 of SEQ ID NO: 9 and no more than amino acids 6–297 of SEQ ID NO: 9.

10. The method of claim 5, wherein the amino acid sequence derived from hepatitis C virus consists of no less than amino acids 13–290 of SEQ ID NO: 9, and no more than amino acids 9–294 of SEQ ID NO: 9.

11. The method of claim 5, wherein said amino acid sequence derived from hepatitis C virus consists of amino acids 11–292 of SEQ ID NO: 9.

12. The method of claim 5, wherein said polypeptide comprises at least one marker group.

13. The method of claim 5, wherein at least one sulfhydryl group in said polypeptide has been modified covalently.

14. Reagent kit useful in determining an antibody against hepatitis C virus, comprising at least two polypeptides, each of which has an amino acid sequence which consists of (i) at least amino acids 21–282 of SEQ ID NO: 9, and no more than amino acids 1–302 of SEQ ID NO: 9, and (ii) an amino acid sequence of less than 20 amino acids which is not found in hepatitis C virus, wherein (ii) is concatenated to the N-terminus or to the C-terminus of the amino acid sequence of (i), wherein at least one of said polypeptides is bound to or is bindable to a solid phase, and another of said polypeptides is labelled.

15. Reagent kit useful in determining antibodies against hepatitis C virus in a sample, comprising a polypeptide, the amino acid sequence of which consists of (i) at least amino acids 21–282 of SEQ ID NO: 9, and no more than amino acids 1–302 of SEQ ID NO: 9, and (ii) an amino acid sequence of less than 20 amino acids which is not found in hepatitis C virus, wherein (ii) is concatenated to the N-terminus or to the C-terminus of the amino acid sequence of (i), bound to orbindable to a solid phase, and a labelled antibody which specifically binds to said polypeptide.

\* \* \* \* \*